(12) United States Patent
Adejare et al.

(10) Patent No.: US 8,735,590 B2
(45) Date of Patent: May 27, 2014

(54) BICYCLO-HEPTAN-2-AMINES

(76) Inventors: Adeboye Adejare, Mantua, NJ (US); Zeynep Ates-Alagoz, Drexel Hill, PA (US); Boyenoh Gaye, Philadelphia, PA (US)

( * ) Notice: Subject to any disclaimer, the term of this patent is extended or adjusted under 35 U.S.C. 154(b) by 168 days.

(21) Appl. No.: 13/354,426

(22) Filed: Jan. 20, 2012

(65) Prior Publication Data
US 2012/0190710 A1 Jul. 26, 2012

Related U.S. Application Data

(60) Provisional application No. 61/434,988, filed on Jan. 21, 2011.

(51) Int. Cl.
*C07D 211/26* (2006.01)
*C07D 309/12* (2006.01)

(52) U.S. Cl.
USPC ............ 546/229; 549/419; 514/331; 514/460

(58) Field of Classification Search
USPC .................... 546/229; 549/419; 514/331, 460
See application file for complete search history.

(56) References Cited

U.S. PATENT DOCUMENTS 3,740,405 A * 6/1973 Kraft ............................... 546/38

* cited by examiner

*Primary Examiner* — David K O Dell
(74) *Attorney, Agent, or Firm* — Fox Rothschild LLP

(57) ABSTRACT

The present invention provides bicyclo-heptan-2-amines that selectively bind to the sigma-2 receptor and are useful in the treatment of diseases related to the sigma-2 receptor, for example, cancer and neurological disorders.

17 Claims, 7 Drawing Sheets

Schema 1. a) Mg, I, THF  b) NaN₃, TFA, CHCl₃  c) LiAlH₄, THF  d) TEA, Et-OH

FIG. 2

Table 2. *In vitro* binding affinities of novel compounds 5a-c for 5-HT$_{2A}$, D$_1$, D$_2$, DAT, KOR, MOR, NET, SERT, Sigma-1, and Sigma-2 receptors

| Comp. | 5HT2A (nM) | D1 (nM) | D2 (nM) | DAT (nM) | KOR (nM) | MOR (nM) | NET (nM) | NMDA PCP Site (nM) | SERT (nM) | Sigma 1 (nM) | Sigma 2 (nM) |
|---|---|---|---|---|---|---|---|---|---|---|---|
| 5a 16552 | >10,000 | >10,000 | >10,000 | 1,480 | 3,435 | >10,000 | >10,000 | >10,000 | >10,000 | >10,000 | 9.6 |
| 5b 16553 | >10,000 | >10,000 | >10,000 | 4,693 | 2,477 | 4,136 | >10,000 | >10,000 | >10,000 | >10,000 | 16 |
| 5c 16557 | >10,000 | >10,000 | >10,000 | 3,161 | 1,238 | 3,038 | >10,000 | >10,000 | >10,000 | >10,000 | 5.5 |

Toxicity (% of untreated control) of novel sigma-2 ligands (A) and Memantine (B) on MDCK cells (24 h treatment; n=3).

Toxicity (% of untreated control) of novel sigma-2 ligands (A) and Memantine (B) on N2a cells (24 h treatment; n=3).

Cytotoxicity (% of untreated control) of novel sigma-2 ligands on U-138 glioma cells (24 h treatment; n=3).

Cytotoxicity (% of untreated control) of novel sigma-2 ligands on MCF-7 cells compared with doxorubicin (24 h treatment; n=3).

BICYCLO-HEPTAN-2-AMINES

CROSS-REFERENCE TO RELATED APPLICATIONS

The present application claims priority under 35 U.S.C. §119(e) to Provisional Patent Application Ser. No. 61/434,988, filed Jan. 21, 2011, the contents of which are hereby incorporated by reference in its entirety.

FIELD OF THE INVENTION

The present invention relates to bicyclo-heptan-2-amines including, for example, (±)-2-Phenyl-N-(3-(piperidin-1-yl)propyl)bicyclo[2.2.1]heptan-2-amine, (±)-2-(4-Fluorophenyl)-N-(3-(piperidin-1-yl)propyl)bicyclo[2.2.1]heptan-2-amine, and (±)-2-(4-Fluorophenyl)-N-(3-(tetrahydro-2H-pyran-2-yloxy)propyl)bicyclo[2.2.1]heptan-2-amine. These compounds can selectively target the Sigma-2 receptor and are useful in the treatment of cancer, disorders of cell proliferation and neurological disorders.

BACKGROUND OF THE INVENTION

Cancer is a leading cause of death worldwide. In the United Stated alone, cancer accounts for about 500,000 deaths per year, and the American Cancer Society estimates that in 2010 approximately 1.5 million new cases of cancer were diagnosed. Cancer treatment modalities include chemotherapy, biologics, external beam radiation and surgical excision. Traditional cancer chemotherapy is nonspecific and targets all rapidly dividing cells, resulting in undesirable side effects. In addition, tumors can become resistant to chemotherapy. Biologics afford greater selectivity, but these agents can stimulate an immune response. For some subjects, the symptoms may be relatively minor, but for others, the symptoms are severe and may result in an inability to continue treatment. Moreover, because biologics are large molecules, they are more challenging and costly to manufacture and/or formulate than small molecule agents, and they generally must be administered intravenously in a clinical setting. External beam radiation and surgery can only target known tumor sites and are ineffective against undetectable metastatic lesions. There is a continuing need for chemotherapeutic agents that selectively target tumor cells.

SUMMARY OF THE INVENTION

The present invention provides compounds of Formula 1:

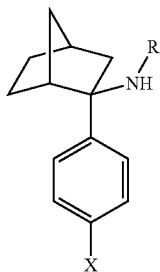

or pharmaceutically acceptable salt forms, wherein constituent members are defined herein. In some embodiments, X is a hydrogen, an alkyl, an alcohol or a halogen; in some embodiments, R is a 3-(piperidin-1-yl)alkyl group or a 3-(tetrahydro-2H-pyran-2-yloxy)alkyl group. Exemplary compounds of Formula 1 include 2-Phenyl-N-(3-(piperidin-1-yl)propyl)bicyclo[2.2.1]heptan-2-amine; 2-(4-Fluorophenyl)-N-(3-(piperidin-1-yl)propyl)bicyclo[2.2.1]heptan-2-amine; and 2-(4-Fluorophenyl)-N-(3-(tetrahydro-2H-pyran-2-yloxy)propyl)bicyclo[2.2.1]heptan-2-amine.

Also provided are compounds of Formula II:

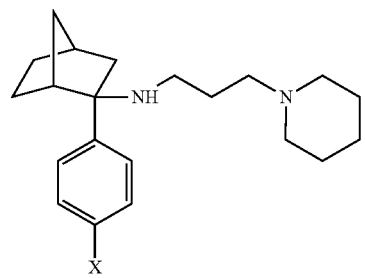

or pharmaceutically acceptable salt forms, wherein constituent members are defined herein. In some embodiments, X is a hydrogen, an alkyl, an alcohol or a halogen.

Also provided are compounds of Formula III:

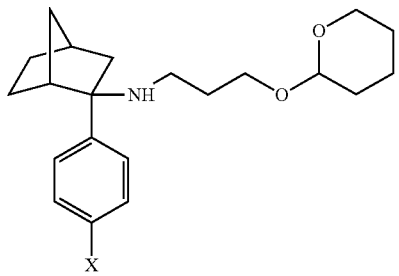

or pharmaceutically acceptable salt forms, wherein constituent members are defined herein. In some embodiments, X is a hydrogen, an alkyl, an alcohol or a halogen. The present compounds that contain asymmetrically substituted carbon atoms can be isolated in optically active or racemic forms.

Also provided are methods of treatment. In some embodiments, a method of treating cancer is provided, the method comprising administering to a subject a therapeutically effective amount of any of the compounds of Formula I, II or III. In some embodiments, the cancer can be breast cancer or glioma. In some embodiments, a method of treating a neurological disorder is provided, the method comprising administering to a subject a therapeutically effective amount of any of the compounds of Formula I, II or III. In some embodiments, the cancer can be Parkinson's disease. Regardless of the disease or disorder, the methods of treatment can further comprise the step of identifying a subject amenable to treatment.

The details of one or more embodiments of the invention are set forth in the accompanying drawings and the description below. Other features, objects and advantages of the invention will be apparent from the description and drawings and from the claims.

BRIEF DESCRIPTION OF THE DRAWINGS

FIG. 2 is a table showing the in vitro binding affinities of compounds 5a, 5b and 5c for 5-HT$_{2A}$, D$_1$, D$_2$, DAT, KOR, MOR, NET, SERT, sigma-1, and sigma-2 receptors.

DETAILED DESCRIPTION

Figure 1:
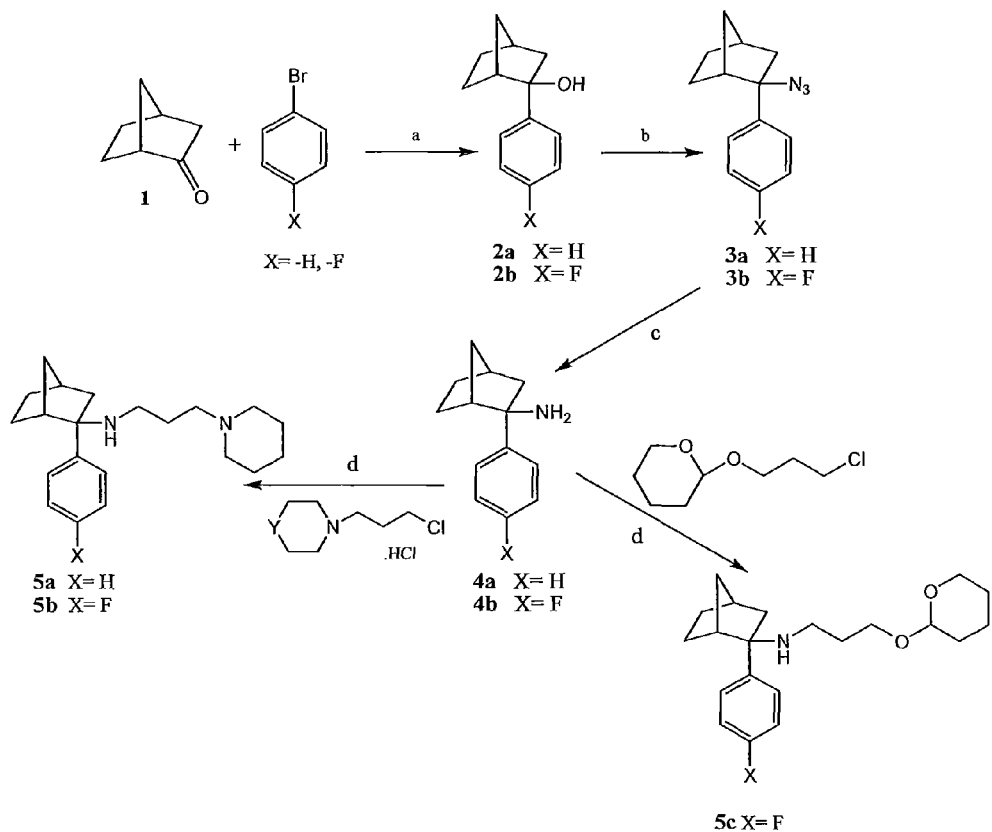
FIG. 1 depicts the synthetic routes for compounds 5a, 5b and 5c.

The present invention is based, in part, on our discovery of compounds that selectively bind the sigma-2 receptor; treatment of cancer cell lines with the compounds resulted in a dose-dependent reduction in cell viability. Accordingly, the compositions of the invention include bicyclo-heptan-2-amines and pharmaceutical formulations including bicyclo-heptan-2-amines. The methods of the invention include methods of administering the compounds to treat cancer. The therapeutic methods described herein can be carried out in connection with other cytotoxic therapies (e.g., chemotherapy, hormone therapy, radiotherapy, and antibody-based therapies).

Sigma (σ) receptors are drug-binding proteins that are present in the central nervous system, endocrine, immune, reproductive, liver and kidney tissues. There are two subtypes, designated sigma-1 and sigma-2, that differ based on their pharmacology, functions and molecular size. The sigma-1 receptor is a 25,000 Da polypeptide with one putative trans membrane region. The gene encoding the sigma-1 receptor has been cloned and the amino acid sequence has no homology to any known human protein. The sigma-2 receptor has a molecular weight of about 18,000-21,500 Da. The gene encoding the sigma-2 receptor has not yet been cloned. Both receptor subtypes have been shown to have moderate affinity for neuroleptics with haloperidol exhibiting the highest affinity for both sites. Sigma-1 receptors exhibit high affinity for (+)-pentazocine, (+)-SKF-10,047 and other (+)-benzomorphans, whereas sigma-2 receptors have low affinity for these compounds.

Both sigma-1 and sigma-2 receptors are expressed in high density in a variety of tumor cell lines including neuroblastoma, glioma, melanoma, breast, prostate and lung carcinoma cell lines. Agonists to the sigma-2 receptor have antiproliferative and cytotoxic effects and have been reported to give a caspase-independent cell death in tumor cells. Sigma-2 receptor agonists have also been reported to affect calcium ion (e.g., Ca$^{2-}$) release from the endoplasmic reticulum and the inward rectifying potassium ion (e.g., K$^+$) channels in the heart. The subcellular localization of the receptor probably includes lysosomes, mitochondria, endoplasmic reticulum, and the plasma membrane. The endogenous ligand(s) to the receptor is not known but some data suggest that the ligand(s) is internalized, in part, by the endocytotic pathway. It has also been suggested that the sigma-2 receptor may be a histone binding protein.

Certain sigma receptor ligands have been shown to induce morphological changes in human neuronal and nonneuronal cell lines that contain sigma-1 and sigma-2 receptors. Sigma receptor ligands have also been shown to induce cell death by apoptosis in human SK—N—SH neuroblastoma cells. Examples of sigma-2 ligands that have been shown to induce apoptosis include ibogaine, CB-64D, and non-specific sigma receptor ligand haloperidol. In contrast, sigma-1-selective ligands, such as (+)-pentazocine and dextrallorphan, or ligands for other receptors such as opioid and dopamine receptors, had little or no effect on cell viability. Sigma ligands have been shown to inhibit proliferation of mammary and colon carcinoma cell lines and induce apoptosis in colon and mammary adenocarcinoma cells. Moreover, certain sigma-2 receptor agonists exhibited similar potency in tumors expressing the wild type or mutant p53, which typically show little or no response to agents that induce apoptosis.

The compounds described herein can function as selective sigma-2 receptor ligands, that is, the molecules are capable of specifically binding a sigma-2 receptor. A ligand exhibits "specific binding" if: 1) it exhibits a threshold level of binding activity as specified below (e.g., a ligand disclosed herein can bind to a sigma-2 receptor with at least or about 1.5-fold greater affinity than it binds a polypeptide that is unrelated to the sigma-2 receptor), and/or 2) it does not significantly bind related target molecules (e.g., another sigma receptor, such as the sigma-1 receptor) or unrelated target molecules (e.g., a receptor for a naturally occurring growth factor, such as NGF or GGF). The binding affinity of a ligand can be readily determined by one of ordinary skill in the art, for example, by Scatchard analysis (Scatchard, Ann. NY Acad. Sci. 51: 660-672, 1949). For example, a ligand disclosed herein can bind to its target with at least or about 1.5-fold, 2-fold, 5-fold, 10-fold, 100-fold, 10$^3$-fold, 10$^4$-fold, 10$^5$-fold, 10$^6$-fold or greater affinity for the target than for a closely related or unrelated polypeptide. A ligand can bind its target with high affinity (e.g., about 10$^{-4}$M or less, 10$^{-7}$M or less, 10$^{-9}$M or less, or with subnanomolar affinity (0.9, 0.8, 0.7, 0.6, 0.5, 0.4, 0.3, 0.2, 0.1 nM or even less). Ligands can also be described or specified in terms of their binding affinity to a target, for example, binding affinities include those with a Kd less than or less than about 5×10$^{-2}$ M, 10$^{-2}$ M, 5×10$^{-3}$ M, 10$^{-3}$ M, 5×10$^{-4}$ M, 10$^{-4}$ M, 5×10$^{-5}$ M, 10$^{-5}$ M, 5×10$^{-6}$ M, 10$^{-6}$ M, 5×10$^{-7}$ M, 10$^{-7}$ M, 5×10$^{-8}$ M, 10$^{-8}$ M, 5×10$^{-9}$ M, 10$^{-9}$ M, 5×10$^{-10}$ M, 10$^{-10}$ M, 5×10$^{-11}$ M, 10$^{-11}$ M, 5×10$^{-12}$ M, 10$^{-2}$M, 5×10$^{-13}$ M, 10$^{-13}$ M, 5×10$^{-14}$ M, 10$^{-14}$ M, 5×10$^{-15}$ M, or 10$^{-15}$ M, or less. In some embodiments, the ligands disclosed herein do not bind to known related molecules. In other embodiments, the ligands disclosed herein can bind to orthologs, homologs, paralogs, or variants, or combinations and subcombinations thereof, of their targets.

Ligands may be screened against known related target polypeptides to identify a ligand that specifically binds the target. Ligands may also be screened for their ability to compete with other unrelated ligands for binding to a particular target. Exemplary screening assays are described in the National Institute of Mental Health Psychoactive Drug Screening Program Assay Protocol Book, which is herein incorporated by reference. The Assay Protocol Book can be accessed on the World-Wide Web at http://pdsp.med.unc.edu/UNC-CH%20Protocol%20Book.pdf. In these assays, test ligands are assayed for the ability to reduce the binding of a known radiolabeled ligand to a particular receptor. The receptor can be partially or substantially purified. In other embodiments, the specific binding activity can be monitored by cell-based methods in which down-stream, functional effects are noted, e.g., $Ca^{2-}$ release or induction of apoptosis.

While we believe we understand certain events that occur in the course of ligand binding to the sigma-2 receptor, the compositions of the present invention are not limited to those that work by affecting any particular cellular mechanism. Thus, in some embodiments, a compound may act as sigma-2 agonist, for example, by stimulating the activity of the sigma-2 receptor that is normally stimulated by a naturally occurring substance. In some embodiments, a compound may act as a partial agonist, for example, by binding to and stimulating the activity of the sigma-2 receptor, but may have only partial efficacy relative to that of a full agonist. In some embodiments, a compound may act as a sigma-2 antagonist, for example, by inhibiting or blocking the activity of the sigma-2 receptor that is normally stimulated by a naturally occurring substance.

Compounds and Structures

The present invention provides, inter alia, compounds that specifically bind to the sigma-2 receptor, e.g., a sigma-2 ligand, and are useful, for example, in the treatment of various diseases such as those associated with sigma-2 receptor expression or activity. Compounds of certain embodiments of the invention are bicyclo-heptan-2-amines. More specifically, compounds of certain embodiments of the invention conform to Formula I:

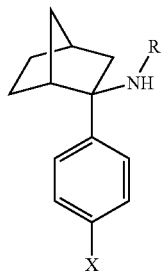

where X is a hydrogen, an alkyl, an alcohol or a halogen, and R is (a) a 3-(piperidin-1-yl)alkyl group or (b) a 3-(tetrahydro-2H-pyran-2-yloxy)alkyl. In certain embodiments, R is 3-(piperidin-1-yl)propyl, and in certain other embodiments, R is 3-(tetrahydro-2H-pyran-2-yloxy)propyl.

With reference to paragraph [0017], in the case of (a), where R is 3-(piperidin-1-yl)propyl, the compounds of certain embodiments of the invention conform to Formula II:

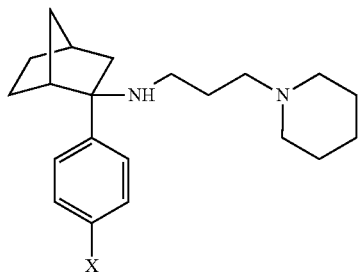

where X is a hydrogen, an alkyl, an alcohol or a halogen.

In Formula II, where X is a hydrogen, the compound is ±2-Phenyl-N-(3-(piperidin-1-yl)propyl)bicyclo[2.2.1]heptan-2-amine.

In Formula II, where X is fluorine, the compound is ±2-(4-Fluorophenyl)-N-(3-(piperidin-1-yl)propyl)bicyclo[2.2.1]heptan-2-amine.

With reference to paragraph [0017], in the case of (b), where R is 3-(tetrahydro-2H-pyran-2-yloxy)propyl, the compounds of certain embodiments of the invention conform to Formula III:

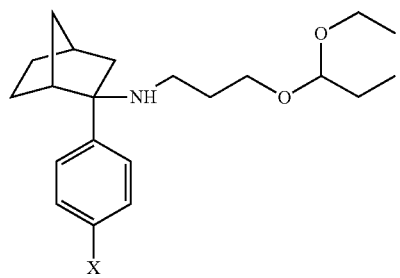

where X is a hydrogen, an alkyl, an alcohol or a halogen.

In Formula III, where X is fluorine, the compound is 2-(4-Fluorophenyl)-N-(3-(tetrahydro-2,1-pyran-2-yloxy)propyl)bicyclo[2.2.1]heptan-2-amine.

Substituents of compounds of the invention may be disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl. The term "substituents" refers to a group "substituted" on, for example, an alkyl, cycloalkyl, alkenyl, alkynyl, aralkyl, heteroaralkyl, heterocyclyl, heterocycloalkenyl, cycloalkenyl, aryl, or heteroaryl group at any atom of that group. In one aspect, the substituents on a group are independently any one single, or any subset of, the aforementioned substituents. In another aspect, a substituent may itself be substituted with any one of the above substituents.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Examplary alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "halo" or "halogen" includes fluoro, chloro, bromo, and iodo. As used herein, the term "hydroxyl" is intended to mean the group —OH.

The compounds described herein, including those conforming to any formula, can be asymmetric (e.g., having one or more stereocenters). All stereoisomers, such as enantiomers and diastereomers, are intended unless otherwise indicated. The present compounds that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated for the present compounds. Cis and trans geometric isomers of the present compounds are described and may be isolated as a mixture of isomers or as separated isomeric forms.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention also include all isotopes of atoms occurring in the intermediate or final compounds. Isotopes include those atoms having the same atomic number but different mass numbers. For example, isotopes of hydrogen include tritium and deuterium.

The term, "compound," as used herein with respect to any compound conforming to one of Formulas I-III, is meant to include all stereoisomers, geometric iosomers, tautomers, and isotopes of the structures depicted. All compounds, and pharmaceutically acceptable salts thereof, are also meant to include solvated or hydrated forms.

The compounds of the present invention can be prepared in a variety of ways known to one of ordinary skill in the art of organic synthesis. The compounds of the present invention can be synthesized using the methods as hereinafter described below, together with synthetic methods known in the art of synthetic organic chemistry or variations thereon as appreciated by one of ordinary skill in the art.

The present compounds can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by one of ordinary skill in the art by routine optimization procedures.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art. The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. In general, "pharmaceutically acceptable salts" refer to derivatives of the disclosed compounds wherein the parent compound is modified by converting an existing acid or base moiety to its salt form. "Pharmaceutically acceptable" generally encompasses those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Methods of Treatment

The compounds disclosed herein are generally and variously useful for treatment of cancer. A patient is effectively treated whenever a clinically beneficial result ensues. This may mean, for example, a complete resolution of the symptoms of a disease, a decrease in the severity of the symptoms of the disease, or a slowing of the disease's progression. These methods can further include the steps of a) identifying a subject (e.g., a patient and, more specifically, a human patient) who has cancer; and b) providing to the subject a composition comprising a compound described herein, such as any pharmaceutically acceptable salt of such a compound. An amount of such a compound provided to the subject that results in a complete resolution of the symptoms of a disease, a decrease in the severity of the symptoms of the disease, or a slowing of the disease's progression is considered a therapeutically effective amount. The present methods may also include a monitoring step to help optimize dosing and scheduling as well as predict outcome. For example, monitoring can be used to detect the onset of drug resistance and to rapidly distinguish responsive patients from nonresponsive patients. Where there are signs of resistance or nonresponsiveness, a physician can choose an alternative or adjunctive agent before the tumor develops additional escape mechanisms.

Patients amenable to treatment include patients with any of a wide variety of cancers or neoplastic disorders, including, for example, without limitation, breast cancer, hematological cancers such as myeloma, leukemia and lymphoma (e.g., Burkitt lymphoma, non-Hodgkin lymphoma, Hodgkin lymphoma, and acute T cell leukemia) neurological tumors such as brain tumors, e.g., gliomas, including astrocytomas or glioblastomas, melanomas, lung cancer, head and neck cancer, thyroid cancer, gastrointestinal tumors such as stomach, colon or rectal cancer, liver cancer, pancreatic cancer, genitourinary tumors such ovarian cancer, vaginal cancer, vulval cancer, endometrial cancer, bladder cancer, kidney cancer, testicular cancer, prostate cancer, or penile cancer, bone tumors, vascular tumors, and skin cancers such as basal cell carcinoma, squamous cell carcinoma and melanoma.

The compounds of the invention are also generally useful for the treatment of neurological disorders. For example, the compositions are useful for treating conditions associated with abnormal function, e.g., overactivation, of NMDA receptors on cells of various types, such as neurons and glutamate-dependent tumor cells. Such conditions can include cerebral ischemia, stroke, brain trauma, brain tumors, Alzheimer's disease, Parkinson's disease, epilepsy and other convulsive disorders, schizophrenia, acute and chronic neuropathic pain, sleep disorders, drug addiction (e.g., addiction to morphine and other opiates), the psychological aspects of depression, vision disorders (e.g., retinal disorders such as macular degeneration), movement disorders, ethanol withdrawal, anxiety, memory dysfunction, learning disabilities, and neurofibromatoses (e.g., neurofibromatosis type 1 (NF-1) and memory- and learning-deficiencies associated with NF-1)).

The methods disclosed herein can be applied to a wide range of species, e.g., humans, non-human primates (e.g., monkeys), horses or other livestock, dogs, cats or other mammals kept as pets, rats, mice, or other laboratory animals. The compounds described herein are useful in therapeutic compositions and regimens or for the manufacture of a medicament for use in treatment of diseases or conditions as described herein (e.g., a cancer disclosed herein).

Administration and Formulation

The compounds described herein can be administered directly to a mammal, which we may also refer to as a "subject" or "patient." Generally, the compounds can be suspended in a pharmaceutically acceptable carrier (e.g., physiological saline or a buffered saline solution) to facilitate their delivery (e.g., by intravenous administration).

As described above, the compounds of the present invention can be prepared in a variety of ways known to one of ordinary skill in the art of chemical synthesis. The present compounds can be prepared from readily available starting materials using the following general methods and procedures. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by one of ordinary skill in the art by routine optimization procedures.

Regardless of their original source or the manner in which they are obtained, the compounds of the invention can be formulated in accordance with their use. For example, the compounds can be formulated within compositions for application to cells in tissue culture or for administration to a patient. When employed as pharmaceuticals, any of the present compounds can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

This invention also includes pharmaceutical compositions which contain, as the active ingredient, one or more of the compounds described herein in combination with one or more pharmaceutically acceptable carriers. In making the compositions of the invention, the active ingredient is typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. As is known in the art, the type of diluent can vary depending upon the intended route of administration. The resulting compositions can include additional agents, such as preservatives. The compounds may also be applied to a surface of a device (e.g., a catheter) or contained within a pump, patch, or other drug delivery device. The compounds of the invention can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formulary). In preparing a formulation, the active compound can be milled to provide the appropriate particle size prior to combining with the other ingredients. If the active compound is substantially water insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The pharmaceutical compositions can be formulated so as to provide quick, sustained or delayed release of the active ingredient after administration to the patient by employing procedures known in the art.

The compositions can be formulated in a unit dosage form, each dosage containing, for example, from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein and/or known in the art. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner. The compositions administered to a patient can be in the form of one or more of the pharmaceutical compositions described above. These compositions can be sterilized by conventional sterilization techniques or may be sterile filtered. Aqueous solutions can be packaged for use as is or lyophilized, the lyophilized preparation being combined with a sterile aqueous carrier prior to administration. The pH of the compound preparations typically will be between about 3 and 11, for example, between about 5 to 9, between 6 and 7, between 7 and 8. It will be understood that use of certain of the foregoing excipients, carriers, or stabilizers could result in the formation of pharmaceutical salts.

The proportion or concentration of the compounds of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration.

The therapeutic dosage of the compounds of the present invention can vary according to, for example, the particular use for which the treatment is made, the manner of administration of the compound, the health and condition of the patient, and the judgment of the attending clinician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. In some embodiments, the dose can be, for example, 1 mg/kg, 2 mg/kg, 5 mg/kg, 10 mg/kg, 20 mg/kg, 50 mg/kg or 100 mg/kg. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Any composition described herein can be administered to any part of the host's body for subsequent delivery to a target cell. A composition can be delivered to, without limitation, the brain, the cerebrospinal fluid, joints, nasal mucosa, blood, lungs, intestines, muscle tissues, skin, or the peritoneal cavity of a mammal. In terms of routes of delivery, a composition can be administered by intravenous, intracranial, intraperitoneal, intramuscular, subcutaneous, intramuscular, intrarectal, intravaginal, intrathecal, intratracheal, intradermal, or transdermal injection, by oral or nasal administration, or by gradual perfusion over time. In a further example, an aerosol preparation of a composition can be given to a host by inhalation.

The dosage required will depend on the route of administration, the nature of the formulation, the nature of the patient's illness, the patient's size, weight, surface area, age, and sex, other drugs being administered, and the judgment of the attending clinicians. Suitable dosages are in the range of 0.01-1,000 mg/kg. Wide variations in the needed dosage are to be expected in view of the variety of cellular targets and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the compounds in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, a compound can be administered once a week (for, for example, 4 weeks to many months or years); once a month (for, for example, three to twelve months or for many years); or once a year for a period of 5 years, ten years, or longer. It is also noted that the frequency of treatment can be variable. For example, the present compounds can be administered once (or twice, three times, etc.) daily, weekly, monthly, or yearly.

An effective amount of any composition provided herein can be administered to an individual in need of treatment. The term "effective" as used herein refers to any amount that induces a desired response while not inducing significant toxicity in the patient. Such an amount can be determined by assessing a patient's response after administration of a known amount of a particular composition. In addition, the level of toxicity, if any, can be determined by assessing a patient's clinical symptoms before and after administering a known amount of a particular composition. It is noted that the effective amount of a particular composition administered to a patient can be adjusted according to a desired outcome as well as the patient's response and level of toxicity. Significant toxicity can vary for each particular patient and depends on multiple factors including, without limitation, the patient's disease state, age, and tolerance to side effects.

Any method known to those in the art can be used to determine if a particular response is induced. Clinical methods that can assess the degree of a particular disease state can be used to determine if a response is induced. The particular methods used to evaluate a response will depend upon the nature of the patient's disorder, the patient's age, and sex, other drugs being administered, and the judgment of the attending clinician.

The compounds may also be administered with another therapeutic agent, such as a cytotoxic agent, or cancer chemotherapeutic. Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

The pharmaceutical compositions can also include other therapeutic antibodies, e.g., antibodies that recognize additional cellular targets. Exemplary immunoglobulins are listed below. Each immunoglobulin is identified by its proper name and its trade name. Numbers in parenthesis beginning with "DB" refer to the identifiers for each antibody on The DrugBank database available at the University of Alberta. The DrugBank database is described in Wishart D S, Knox C, Guo A C, et al. (2008). "DrugBank: a knowledgebase for drugs, drug actions and drug targets". *Nucleic Acids Res.* 36 (Database issue): D901-6 and can be accessed at www.drugbank.ca. Useful immunoglobulins include: Abciximab (ReoPro™) (DB00054), the Fab fragment of the chimeric human-murine monoclonal antibody 7E3, the synthesis of which is described in EP0418316 (A1) and WO8911538 (A1), which are herein incorporated by reference; Adalimumab (Humira™) (DB00051), a fully human monoclonal antibody that binds to Tumor Necrosis Factor alpha (TNF-α) and blocks TNF-α binding to its cognate receptor; alemtuzumab (Campath™) (DB00087), a humanized monoclonal antibody that targets CD52, a protein present on the surface of mature lymphocytes, used in the treatment of chronic lymphocytic leukemia (CLL), cutaneous T cell lymphoma (CTCL) and T-cell lymphoma; basiliximab (Simulect™) (DB00074), a chimeric mouse-human monoclonal antibody to the a chain (CD25) of the IL-2 receptor; bevacizumab (Avastin™) (DB00112) a humanized monoclonal antibody that recognizes and blocks vascular endothelial growth factor (VEGF), the chemical signal that stimulates angiogenesis, the synthesis of which is described in Presta L G, Chen H, O'Connor S J, et al Humanization of an anti-vascular endothelial growth factor monoclonal antibody for the therapy of solid tumors and other disorders. Cancer Res, 57: 4593-9, 1997; certuximab (Erbitux™) (DB00002), a chimeric (mouse/human) monoclonal antibody that binds to and inhibits the epidermal growth factor receptor (EGFR), the synthesis of which is described in U.S. Pat. No. 6,217,866, which is herein incorporated by reference; certolizumab pegol (Cimzia™), a PEGylated Fab' fragment of a humanized TNF-α inhibitor monoclonal antibody; daclizumab (Zenapax™) (DB00111), a humanized monoclonal antibody to the alpha subunit of the IL-2 receptor; eculizumab (Soliris™), a humanized monoclonal antibody that binds to the human C5 complement protein; efalizumab (Raptiva™) (DB00095), a humanized monoclonal antibody that binds to CD11a; gemtuzumab (Mylotarg™) (DB00056) a monoclonal antibody to CD33 linked to a cytotoxic agent, the amino acid sequence of which is described in J Immunol 148:1149, 1991) (Caron P C, Schwartz M A, Co M S, Queen C, Finn R D, Graham M C, Divgi C R, Larson S M, Scheinberg D A. Murine and humanized constructs of monoclonal antibody M195 (anti-CD33) for the therapy of acute myelogenous leukemia. Cancer. 1994 Feb. 1; 73(3 Suppl):1049-56); ibritumomab tiuxetan (Zevalin™) (DB00078), a monoclonal mouse IgG1 antibody ibritumomab in conjunction with the chelator tiuxetan and a radioactive isotope (yttrium$^{90}$ or indium$^{111}$); Infliximab (Remicade™) (DB00065), a chimeric mouse-human monoclonal antibody that binds to tumor necrosis factor alpha (TNF-α), the synthesis of which is described in U.S. Pat. No. 6,015,557, which is herein incorporated by reference; muromonab-CD3 (Orthoclone OKT3™), a mouse monoclonal IgG2a antibody that binds to the T cell receptor-CD3-complex; natalizumab (Tysabri™) (DB00108), a humanized monoclonal antibody against the cellular adhesion molecule α4-integrin, the sequence of which is described in Leger O J, Yednock T A, Tanner L, Horner H C, Hines D K, Keen S, Saldanha J, Jones S T, Fritz L C, Bendig M M. Humanization of a mouse antibody against human α4-integrin: a potential therapeutic for the treatment of multiple sclerosis. Hum Antibodies. 1997; 8(1):3-16; omalizumab (Xolair™) (DB00043), a humanized IgG1k monoclonal antibody that selectively binds to human immunoglobulin E (IgE); palivizumab (Synagis™) (DB00110), a humanized monoclonal antibody (IgG) directed against an epitope in the A antigenic site of the F protein of the Respiratory Syncytial Virus (RSV), the amino acid sequence of which is described in Johnson S, Oliver C, Prince G A, Hemming V G, Pfarr D S, Wang S C, Dormitzcr M, O'Grady J, Koenig S, Tamura J K, Woods R, Bansal G, Couchenour D, Tsao E, Hall W C, Young J F. Development of a humanized monoclonal antibody (MEDI-493) with potent in vitro and in vivo activity against respiratory syncytial virus. J Infect Dis. 1997 November; 176(5): 1215-24; panitumumab (Vectibix™), a fully human monoclonal antibody specific to the epidermal growth factor receptor (also known as EGF receptor, EGFR, ErbB-1 and HER1 in humans); ranibizumab (Lucentis™), an affinity matured anti-VEGF-A monoclonal antibody fragment derived from the same parent murine antibody as bevacizumab (Avastin); rituximab (Rituxan™, Mabthera™) (DB00073), a chimeric monoclonal antibody against the protein CD20, which is primarily found on the surface of B cells; tositumomab (Bexxar™) (DB00081), an anti-CD20 mouse monoclonal antibody covalently bound to $^{131}$I; or trastuzumab (Herceptin™) (DB00072), a humanized monoclonal antibody that binds selectively to the HER2 protein.

The antibodies can include bioequivalents of the approved or marketed antibodies (biosimilars). A biosimilar can be for example, a presently known antibody having the same primary amino acid sequence as a marketed antibody, but may be made in different cell types or by different production, purification or formulation methods. Generally, any deposited materials can be used.

The pharmaceutical compositions may also include or be administered along with a cytotoxic agent, e.g., a substance that inhibits or prevents the function of cells and/or causes destruction of cells. Exemplary cytotoxic agents include radioactive isotopes (e.g., $^{131}$I, $^{125}$I, $^{90}$Y and $^{186}$Re), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic. A non-cytotoxic agent may include a bead, liposome, matrix or particle (see, e.g., U.S. Patent Publications 2003/0028071 and 2003/0032995 which are incorporated by reference herein). Such agents may be conjugated, coupled, linked or associated with an antibody disclosed herein.

Conventional cancer medicaments can be administered with the compositions disclosed herein. Useful medicaments include anti-angiogenic agents, i.e., agents that block the ability of tumors to stimulate new blood vessel growth necessary for their survival. Any anti-angiogenic agent known to those in the art can be used, including agents such as Bevacizumab (Avastin®, Genentech, Inc.) that block the function of vascular endothelial growth factor (VEGF). Other examples include, without limitation, Dalteparin (Fragmin®), Suramin ABT-510, Combretastatin A4 Phosphate, Lenalidomide, LY317615 (Enzastaurin), Soy Isoflavone (Genistein; Soy Protein Isolate) AMG-706, Anti-VEGF antibody, AZD2171, Bay 43-9006 (Sorafenib tosylate), PI-88, PTK787/ZK 222584 (Vatalanib), SU11248 (Sunitinib malate), VEGF-Trap, XL184, ZD6474, Thalidomide, ATN-161, EMD 121974 (Cilenigtide) and Celecoxib (Celebrex®).

Other useful therapeutics include those agents that promote DNA-damage, e.g., double stranded breaks in cellular DNA, in cancer cells. Any form of DNA-damaging agent know to those of skill in the art can be used. DNA damage can typically be produced by radiation therapy and/or chemotherapy. Examples of radiation therapy include, without limitation, external radiation therapy and internal radiation therapy (also called brachytherapy). Energy sources for external radiation therapy include x-rays, gamma rays and particle beams; energy sources used in internal radiation include radioactive iodine (iodine$^{125}$ or iodine$^{131}$), and from strontium$^{89}$, or radioisotopes of phosphorous, palladium, cesium, iridium, phosphate, or cobalt. Methods of administering radiation therapy are well known to those of skill in the art.

Examples of DNA-damaging chemotherapeutic agents include, without limitation, Busulfan (Myleran), Carboplatin (Paraplatin), Carmustine (BCNU), Chlorambucil (Leukeran), Cisplatin (Platinol), Cyclophosphamide (Cytoxan, Neosar), Dacarbazine (DTIC-Dome), Ifosfamide (Ifex), Lomustine (CCNU), Mechlorethamine (nitrogen mustard, Mustargen), Melphalan (Alkeran), and Procarbazine (Matulane).

Other standard cancer chemotherapeutic agents include, without limitation, alkylating agents, such as carboplatin and cisplatin; nitrogen mustard alkylating agents; nitrosourea alkylating agents, such as carmustine (BCNU); antimetabolites, such as methotrexate; folic acid; purine analog antimetabolites, mercaptopurine; pyrimidine analog antimetabolites, such as fluorouracil (5-FU) and gemcitabine (Gemzar®); hormonal antineoplastics, such as goserelin, leuprolide, and tamoxifen; natural antineoplastics, such as aldesleukin, interleukin-2, docetaxel, etoposide (VP-16), interferon alfa, paclitaxel (Taxol®), and tretinoin (ATRA); antibiotic natural antineoplastics, such as bleomycin, dactinomycin, daunorubicin, doxorubicin, daunomycin and mitomycins including mitomycin C; and vinca alkaloid natural antineoplastics, such as vinblastine, vincristine, vindesine; hydroxyurea; aceglatone, adriamycin, ifosfamide, enocitabine, epitiostanol, aclarubicin, ancitabine, nimustine, procarbazine hydrochloride, carboquone, carboplatin, carmofur, chromomycin A3, antitumor polysaccharides, antitumor platelet factors, cyclophosphamide (Cytoxin®), Schizophyllan, cytarabine (cytosine arabinoside), dacarbazine, thioinosine, thiotepa, tegafur, dolastatins, dolastatin analogs such as auristatin, CPT-11 (irinotecan), mitozantrone, vinorelbine, teniposide, aminopterin, caminomycin, esperamicins (See, e.g., U.S. Pat. No. 4,675,187), neocarzinostatin, OK-432, bleomycin, furtulon, broxuridine, busulfan, honvan, peplomycin, bestatin (Ubenimex®), interferon-β, mepitiostane, mitobronitol, melphalan, laminin peptides, lentinan, *Coriolus versicolor* extract, tegafur/uracil, estramustine (estrogen/mechlorethamine).

Additional agents which may be used as therapy for cancer patients include EPO, G-CSF, ganciclovir; antibiotics, leuprolide; meperidine; zidovudine (AZT); interleukins 1 through 18, including mutants and analogues; interferons or cytokines, such as interferons α, β, and γ hormones, such as luteinizing hormone releasing hormone (LHRH) and analogues and, gonadotropin releasing hormone (GnRH); growth factors, such as transforming growth factor-β (TGF-β), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-α & β (TNF-α & β); invasion inhibiting factor-2 (IIF-2); bone morphogenetic proteins 1-7 (BMP 1-7); somatostatin; thymosin-α-1; γ-globulin; superoxide dismutase (SOD); complement factors; and anti-angiogenesis factors.

Useful therapeutic agents include, produgs, e.g., precursors or derivative forms of a pharmaceutically active substance that is less cytotoxic or non-cytotoxic to tumor cells compared to the parent drug and is capable of being converted, either enzymatically or non-enzymatically, into an active or the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use herein include, but are not limited to, those chemotherapeutic agents described above.

In the case of neurological disorders, the compounds of the invention may be administered with another therapeutic agent or a surgical procedure. As is the case for cancer therapeutics, concurrent administration of two or more therapeutic agents for treatment of a neurological disorder does not require that the agents be administered at the same time or by the same route, as long as there is an overlap in the time period during which the agents are exerting their therapeutic effect. Simultaneous or sequential administration is contemplated, as is administration on different days or weeks.

Exemplary therapeutic agents for treating neurological disorders include carbidopa/levodopa, (Sinemet®, Stalevo®); dopamine agonists, e.g, bromocriptine (Parlodel®), pramipexole (Mirapex®) and ropinirole (Requip®); anticholinergics, e.g, trihexyphenidyl, benztropine mesylate and procyclidine; MAO-B inhibitors, e.g., selegiline, deprenyl (Eldepryl®); COMT inhibitors, e.g., entacapone (Comtan®); and other agents such as amantadine, (Symmetrel®) and rivastigmine tartrate (Exelon®); gabapentin (Fanatrex®, Gabarone® and Neurontin®). Exemplary treatments for neuropathic pain include anti-epilepsy drugs, e.g., Gabapentin (Neurontin®) and Pregabalin (Lyrica®) or antidepressants, e.g., tricyclic antidepressants, selective serotonin reuptake inhibitors; serotonin and noradrenergic reuptake inhibitors (SNaRI), e.g., venlafaxine and nefazodone; noradrenergic and specific serotoninergic antidepressants (NaSSA), e.g., mirtazapine; and noradrenaline reuptake inhibitors (NaRI), e.g., reboxetine.

Articles of Manufacture

The compounds described herein can be packaged in suitable containers labeled, for example, for use as a therapy to treat a disease or disorder of cell proliferation (e.g., cancer) or a neurological disorder. The containers can include the compound and one or more of a suitable stabilizer, carrier molecule, flavoring, and/or the like, as appropriate for the intended use. Accordingly, packaged products (e.g., sterile containers containing one or more of the compounds described herein and packaged for storage, shipment, or sale at concentrated or ready-to-use concentrations) and kits, including at least one compound of the invention and instructions for use, are also within the scope of the invention. A product can include a container (e.g., a vial, jar, bottle, bag, or the like) containing one or more compounds of the invention. In addition, an article of manufacture further may include, for example, packaging materials, instructions for use, syringes, buffers or other control reagents for treating or monitoring the condition for which prophylaxis or treatment is required. The product may also include a legend (e.g., a printed label or insert or other medium describing the product's use (e.g., an audio- or videotape)). The legend can be associated with the container (e.g., affixed to the container) and can describe the manner in which the compound therein should be administered (e.g., the frequency and route of administration), indications therefor, and other uses. The compounds can be ready for administration (e.g., present in dose-appropriate units), and may include a pharmaceutically acceptable adjuvant, carrier or other diluent and/or an additional therapeutic agent. Alternatively, the compounds can be provided in a concentrated form with a diluent and instructions for dilution.

EXAMPLES

Example 1

Materials and Methods

Melting points were determined with a MeI-Temp electrothermal apparatus and are uncorrected. The $^1$H, $^{13}$C and $^{19}$F NMR spectra were recorded with a 400 MHz Bruker NMR spectrophotometer with TMS as internal standard and CDCl$_3$ as solvent. The Mass spectra were recorded with a Varian 1200 Triple Quadrupole instrument using electrospray ionization (ESI) technique. Column chromatography was conducted using Merck silica gel, grade 9385, 230-400 mesh, 60 Å. Compound purity was determined by elemental analysis conducted by Galbraith Laboratories, Knoxville, Tenn. The chemical reagents used in the synthesis were purchased from Aldrich, Acros and Alfa Aesar.

The synthetic route, shown in FIG. 1 ("Scheme 1") was based in part on the method described in Geneste et al. (Geneste, P.; Herrmann, P.; Kamenka, J. M.; Pons, A.; New Synthesis of isomers of 1-phenylcyclohexylamines substituted on the cyclohexane ring. *Bulletin De La Societe Chimique de France* 1975, 1619-1626.) and consisted of condensation of a Grignard reagent with norcamphor. Treatment of the resultant tertiary alcohol with trifluoroacetic acid (TFA) in the presence of sodium azide resulted in the tertiary azide, which was then reduced to the corresponding amine with lithium aluminum hydride (LiAlH$_4$) to give intermediates 4. Treatment of these amines with alkyl halogen derivatives in the presence of ethyl alcohol and triethyl amine completed syntheses of the target compounds.

Example 2

Syntheses of compounds 2a-4-a

A mixture of bromobenzene (5.5 ml, 52.2 mmol), magnesium turnings (3.81 g, 157 mmol), and a few iodine crystals was stirred to give Grignard reagent and was added to norcamphor (5.75 g, 52.2 mmol) to give a crude alcohol as a red oil (2a, 9.2 g, 93% yield). Treatment of this alcohol (9.0 g, 47.8 mmol) with TFA (32 ml, 430 mmol) in the presence of sodium azide (9.3 g, 143 mmol) resulted in the tertiary azide as a red oil (3a, 9.3 g, 91% yield), This azide (9.3 g, 40 mmol) was reduced to the corresponding amine with LiAlH$_4$ (2.5 g, 67 mmol) to give (±)-2-phenylbicyclo[2.2.1]heptan-2-amine (4a) as a clear oil (7.8 g, 90% yield). This oil (0.2 g) was purified by preparative TLC developed using a mixture of chloroform and diethyl ether (9:1, v/v) as mobile phase. A pale yellow oil was obtained, which solidified at 0° C. $^1$H NMR (CDCl$_3$): δ ppm 7.3-7.4 (m, 5H), 1.0-2.6 (b, 10H, 4CH$_2$ and 2CH). $^{13}$C NMR (CDCl$_3$): δ 148.3, 128.6, 127.0, 126.4, 64.1, 48.5, 45.2, 37.1, 36.9, 28.8, 24.8; MS (ESI+) m/z: 188 (10%), [M+H], 171 (100%), [M−16]. The amine hydrochloride salt was obtained by bubbling hydrogen chloride gas through the ethyl ether solution. The solvent used for crystallization was the mixture of methanol and ethyl ether to give white crystalline solid; m.p. 243-244° C. Anal. Calcd for compound 4a hydrochloride, C$_{13}$H$_{18}$ClN-0.1H$_2$O: C, 69.23; H, 8.13; N, 6.21. Found: C, 69.22; H, 8.11; N, 6.10.

Example 3

Syntheses of Compounds 2b-4-b

Crude alcohol 2b (9.4 g, 99% yield) was obtained from p-bromofluorobenzene (5.00 ml, 45.5 mmol), magnesium turnings (3.32 g, 137 mmol), and norcamphor (5.00 g, 45.5 mmol) as described for synthesis of compound 2a. $^1$H NMR (CDCl$_3$): δ ppm 7.63-7.43 (m, 2H), 7.15-6.96 (m, 2H), 2.58 (s, 1H), 2.44-2.11 (m, 3H), 1.81-1.26 (m, 7H); $^{13}$C NMR (CDCl$_3$): δ ppm 162.8, 144.89, 127.7, 127.6, 114.9, 114.7, 80.45, 47.6, 46.9, 38.8, 37.6, 29.1, 22.28. Treatment of the alcohol (9.4 g, 46 mmol) with TFA (30.5 ml, 410 mmol) in the presence of sodium azide (8.89 g, 137 mmol) resulted in the tertiary azide as a red oil (3b, 10.5 g, 93.6% yield). The azide (10.5 g, 45.4 mmol) was then reduced to the corresponding amine with LiAlH$_4$ (2.60 g, 68 mmol) to give (±)-2-(4-fluorophenyl)bicyclo[2.2.1]heptan-2-amine (4b) as a clear oil (6.6 g, 70.8% yield). The oil (0.4 g) was purified by preparative TLC developed using a mixture of chloroform and diethyl ether (9:1, v/v) as mobile phase. A pale yellow oil was obtained; this oil solidified at 0° C. $^1$H NMR (CDCl$_3$): δ ppm 7.2 (m, 2H), 6.8 (m, 2H), 1.0-2.6 (b, 10H, 4CH$_2$ and 2CH); $^{13}$C NMR (CDCl$_3$): δ 163.0, 160.4, 128.6, 128.5, 115.3, 115.0, 63.6, 48.7, 45.6, 37.1, 36.8, 28.7, 24.7; $^{19}$F NMR (CDCl$_3$): δ-117.6 ppm. MS (ESI+) m/z: 206 (10%), [M+H], 189 (100%), [M−16]. The amine hydrochloride salt was obtained as described for compound 4a. Anal. Calcd for compound 4b hydrochloride. C$_{13}$H$_{17}$ClFN: C, 64.59: H. 7.09; F, 7.86; N, 5.79. Found: C, 64.30; H, 7.29; F, 7.56; N, 5.62. m.p. 214-216° C.

Example 4

General Procedure for the Syntheses of Compounds 5a, 5b and 5c

The crude base of compound 4, (±)-2-phenylbicyclo[2.2.1]heptan-2-amine or 2-(4-fluoro-phenyl)-bicyclo[2.2.1]hept-2-ylamine (5.4 mmol) and appropriate alkyl halogen derivatives (5.6 mmol) dissolved in ethanol (30 mL) and triethylamine (1 ml, 7.1 mmol), to form a mixture that was heated at 50° C. for 20-48 h. After cooling, the solvent was removed under reduced pressure and the residue was treated with water. The mixture was extracted with ethyl acetate (3×20 mL). Organic phase was separated, dried over sodium sulfate, and purified by column chromatography. Hydrochloride salt of the compound was obtained by bubbling hydrogen chloride gas in the ethyl ether solution of the compound. Fumarate salt was obtained using equal molar amounts of fumaric acid and compound in methanol. The solvent used for crystallization was the mixture of methanol and ethyl ether at 0° C.

Example 5

(±)-2-Phenyl-N-(3-(piperidin-1-yl)propyl)bicyclo[2.2.1]heptan-2-amine (5a)

The compound was prepared from 4a (1.63 g, 6.2 mmol) and 1-(3-chloroethyl)piperidine hydrochloride (1.43 g, 7.2 mmol) according to general procedure and was purified by column chromatography (EtOAc/1-prOH/TEA 8:2:0.2) to give 5a (0.58 g, 21% yield) as a colorless oil. $^1$H NMR (400 MHz, CDCl$_3$) δ ppm 7.37-7.25 (m, 4H), 7.20 (tt, J=6.22, 1.71 Hz, 1H), 2.47 (s, 1H), 2.39-2.14 (m, 8H), 2.14-2.01 (m, 2H), 1.89 (dd, J=12.62 Hz, 1H), 1.78-1.68 (m, 1H), 1.61-1.51 (m, 4H), 1.51-1.25 (m, 8H), 1.05 (dd, J=7.45 Hz, 2H); MS (ESI+) m/z: 313 (100%), [M+H]. Fumarate salt was prepared to give colorless crystals, m.p. 190-192° C. Anal. Calcd. for fumarate salt; C$_{29}$H$_{40}$N$_2$O$_8$.4H$_2$O: C, 63.12; H, 7.45; N, 5.08. Found: C, 63.18; H, 7.42; N, 5.11.

Example 6

(±)-2-(4-Fluorophenyl)-N-(3-(piperidin-1-yl)propyl)bicyclo[2.2.1]heptan-2-amine (5b)

The compound was prepared from 4b (1.08 g, 5.0 mmol) and 1-(3-chloroethyl)piperidine hydrochloride (1.15 g, 5.8 mmol) according to general procedure and was purified by column chromatography (EtOAc/i-prOH/TEA 8:2:0.2) to give 5b (0.60 g, 34% yield) as a colorless oil. $^1$H NMR (400 MHz, CDCl$_3$) δ ppm 7.35-7.25 (m, 2H), 6.99 (t, J=8.59 Hz, 2H), 2.48-1.99 (m, 11H), 1.88-1.68 (m, 2H), 1.62-1.24 (m, 12H), 1.02 (d, J=2.48 Hz, 2H); MS (ESI+) m/z: 331 (100%), [M+H]. Fumarate salt was prepared to give colorless crystals, m.p. 193-195° C. Calcd. for fumarate salt; C$_{29}$H$_{39}$FN$_2$O$_8$.2H$_2$O: C, 61.51; H, 7.01; F, 3.35; N, 4.95. Found: C, 61.50; H, 7.02; F, 3.07; N, 4.97.

Example (±)-7: 2-(4-Fluorophenyl)-N-(3-(tetrahydro-2H-pyran-2-yloxy)propyl)bicyclo[2.2.1]heptan-2-amine (5c)

The compound was prepared from 4b (1.89 g, 9.2 mmol) and 2-(3-chloropropoxy)tetrahydro-2H-pyran (1.5 mL, 9.2 mmol) according to general procedure and was purified by column chromatography (EtOAc) to give 5f (0.81 g, 25% yield) as a colorless oil. $^1$H NMR (400 MHz, CDCl$_3$) δ ppm 7.37-7.26 (m, 2H), 7.06-6.95 (m, 2H), 4.51 (s, 1H), 3.80 (s, 1H), 3.70 (s, 1H), 3.48 (d, J=5.53 Hz, 1H), 3.37 (d, 6.11 Hz, 1H), 2.45 (s, 1H), 2.35 (s, 1H), 2.32-2.21 (m, 1H), 2.21-2.11 (m, 1H), 2.11-2.03 (m, 1H), 1.81 (dd, J=19.13 Hz, 3H), 1.67 (s, 1H), 1.64-1.43 (m, 7H), 1.43-1.26 (m, 3H), 1.03 (d, J=6.97 Hz, 2H); MS (ESI+) m/z: 348 (100%), [M+H]. Fumarate salt was prepared to give colorless crystals, m.p. 163-165° C. Anal. Calcd. for fumarate salt; C$_{25}$H$_{34}$FNO$_6$.3H$_2$O: C, 64.03; F, 4.05; H, 7.43 N, 2.98. Found: C, 63.99; F, 3.88; H, 7.15; N, 2.96.

Example 8

Receptor Binding Analysis

Compounds 5a, 5b and 5c were accepted into the National Institute of Mental Health Psychoactive Drug Screening Program, NIMH-PDSP, National Institutes of Health (NIH). Each compound was evaluated for affinity at human or rat receptors. Sites to be evaluated were chosen based on known or suspected sites of interaction with related compounds. The receptors evaluated, radio-labeled ligand, species and receptor source are depicted in Table 1. Experimental details and procedure can be found through Assay Protocol Book, National Institute of Mental Health Psychoactive Drug Screening Program, University of North Carolina at Chapel Hill.

TABLE 1

Receptors, species, sources and reference compounds

| Receptor | Reference Comp. | Species | Source |
| --- | --- | --- | --- |
| 5-HT$_{2A}$ | Ketanserin | Human | Cloned |
| Dopamine 1 (D1) | SCH23390 | Human | Cloned |
| Dopamine 1 (D2) | N-Methylspiperone | Human | Cloned |
| Dopamine Transporter (DAT) | WIN35428 | Human | Cloned |
| κ-opioid receptors (KOR) | U69593 (2007-07-27) | Rat | Cloned |
| μ-opioid receptors (MOR) | DAMGO (2007-07-27) | Human | Cloned |
| Norepinephrine Transporter (NET) | Nisoxetine | Human | Cloned |
| NMDA PCP Site | MK801 | Rat | Brain |
| Serotonin Transporter (SERT) | Citalopram | Human | Cloned |
| Sigma$_1$ | Pentazocine(+) | Rat | Brain |
| Sigma$_2$ | DTG | Rat | PC12 |

Figure 7:
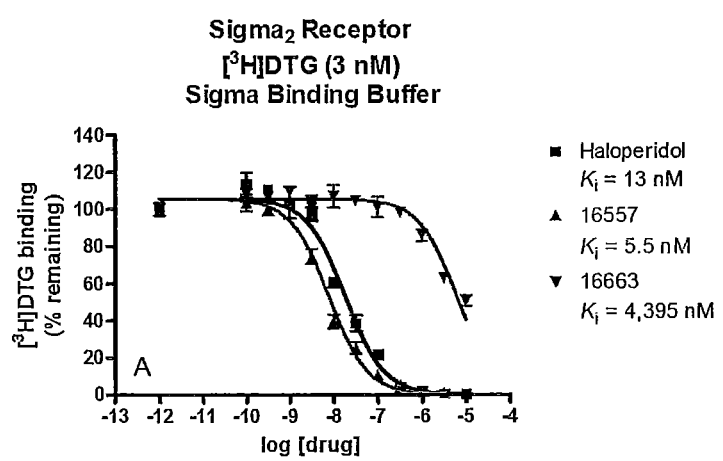
FIG. 7 is a graph depicting the results of an analysis of a sigma-2 receptor competition binding assay for compound 5c ("16557").

In vitro binding affinities of compounds 5a, 5b and 5c for 5-HT$_2$A, D$_1$, D$_2$, DAT, KOR, MOR, NET, SERT, Sigma-1, and Sigma-2 receptors are shown in FIG. 2 (Table 2). Compounds 5a-c showed selective binding to the Sigma-2 receptor in the nanomolar range, with Ki's of 9.6, 16, and 5.5 nM, respectively, for the Sigma-2 receptor and Ki's of >10,000 nM for the Sigma-1 receptor. Concentration-dependent specific binding for compound 5c ("16557") is shown in FIG. 7.

Example 9

Effect of Compounds 5a, 5b and 5c on Cell Viability in Neuronal N2a Cells

We evaluated the effect of compounds 5a, 5b and 5c on cell viability in the neuronal cell line N2a and in the Madin-Darby canine kidney (MDCK) cell line, a blood-brain barrier model. Memantine, an NMDA glutamate receptor antagonist, was used as a negative control.

Mouse Neuro-2a (CCL-131, ATCC) and MDCK (CCL-34, ATCC) were routinely propagated using Eagle's Minimum Essential Medium (EMEM, ATCC), supplemented with 10% fetal bovine serum (FBS, ATCC) and 1% penicillin/streptomycin (Gibco) in 100 cm$^2$ Petri-dishes (Corning) at 37° C. in 5% CO$_2$. Compounds 5a, 5b and 5c were obtained as salts. Stock solutions (1 mM) were prepared in double distilled water. The treatment concentrations for the compounds and the memantine control were 10, 50, 100, 200, 300, and 500 μM. Cells were allowed to attach overnight prior to treatment. H$_2$O$_2$ served as positive control. Working concentrations were prepared immediately prior to treatment by dilution into medium.

Cell viability was assayed using the MTT (3-(4,5-dimethylthiazole-2-yl)-2,5-diphenyltetrazoliumbromide) assay (ATCC) according to manufacturer's instructions. Cells were plated at a concentration of 13,000 to 20,000 cells/well on a 96-well round-bottom plate. MTT assay. The following determinants were optimized for each cell line: plating cell concentration; incubation time with MTT reagent, and incubation time with detergent reagent. Absorbance was recorded at 570 nm by a microtiter plate reader (VICTOR$^3$, PerkinElmer). This experiment was repeated on three separate occasions and results were presented as the mean absorbance±SD.

Figure 3:
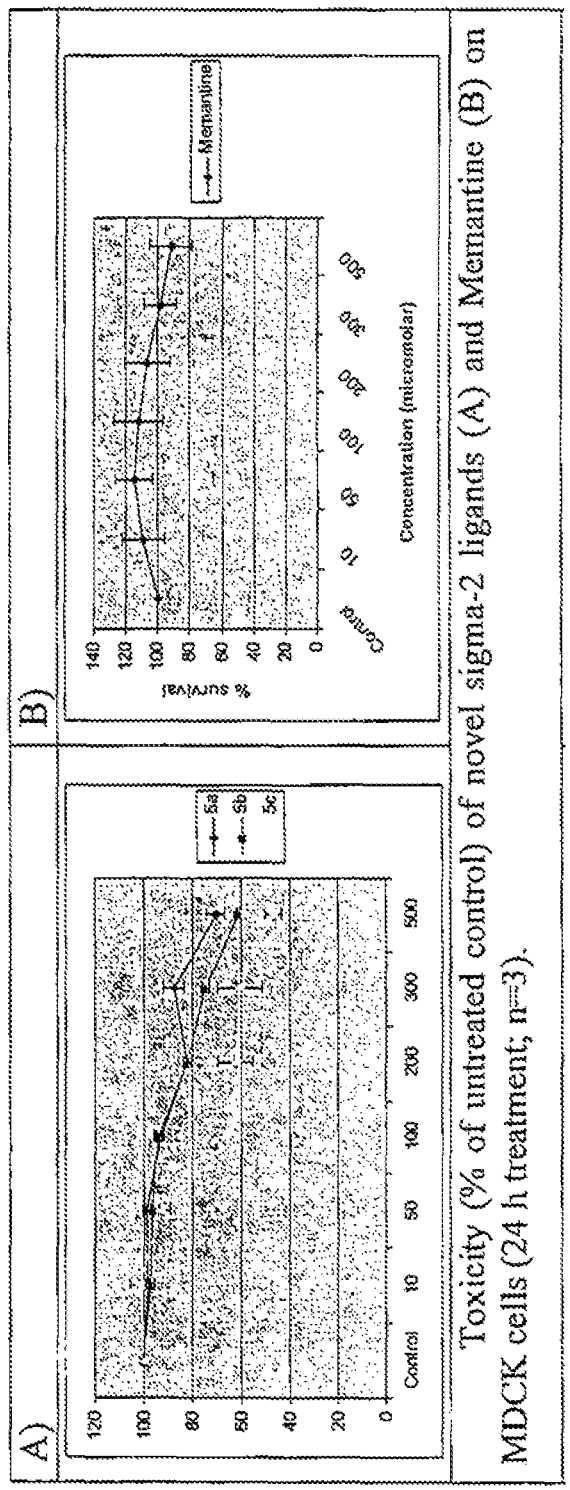
FIGS. 3A and 3B are graphs depicting the results of an analysis of the effect of experimental compounds 5a, 5b and 5c and the negative control compound, memantine, respectively, on cell viability in MDCK cells.
Figure 4:
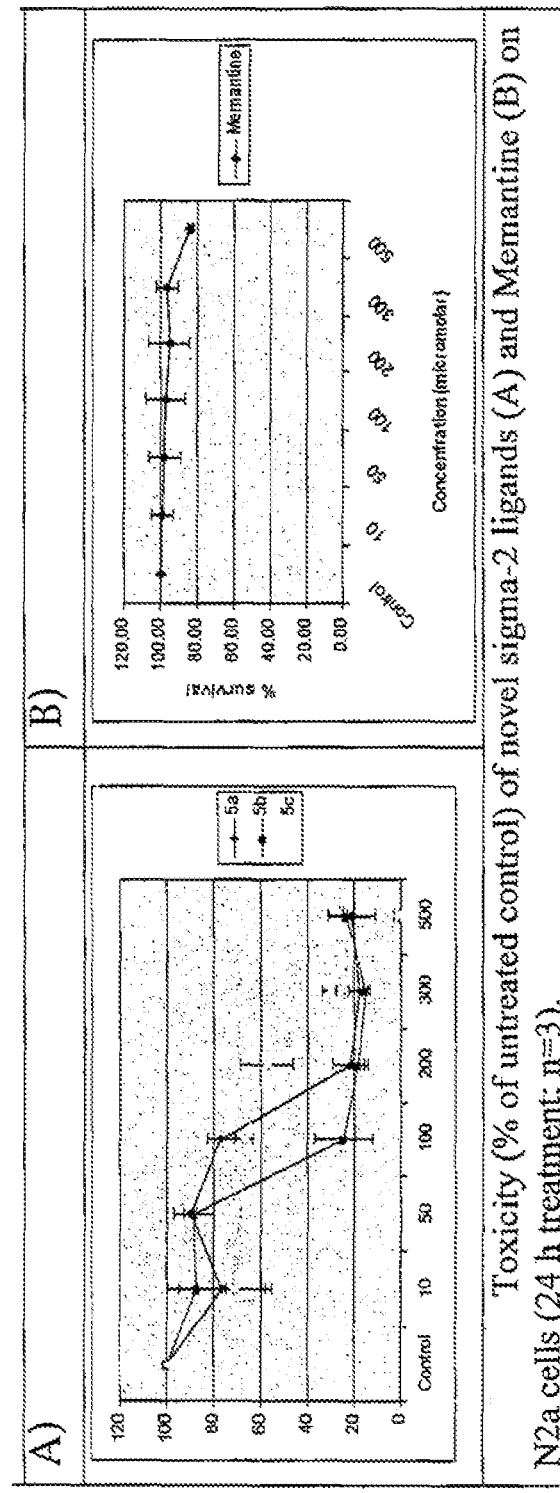
FIGS. 4A and 4B are graphs depicting the results of an analysis of the effect of experimental compounds 5a, 5b and 5c and the negative control compound, memantine, respectively, on cell viability in N2a cells.

As shown in FIG. 3A, compounds 5a, 5b and 5c, had minimal effects on cell viability in MDCK cells. In contrast, as shown in FIG. 4A. compounds 5a, 5b and 5c, showed a dose-dependent reduction in cell viability in N2a cells.

Example 9

Effect of Compounds 5a, 5b and 5c on Cell Viability in Cancer Cell Lines

We also evaluated the effect of compounds 5a, 5b and 5c on the human glioma cell line U-138 and the human breast carcinoma cell line MCF-7. Doxorubicin, a clinically used anticancer compound, served as a positive control.

Cell viability was assayed using the MTT assay essentially as described in Example 8. Adherent cells were trypsinized and placed into 96-well flat bottom tissue culture plates in 100 μl of supplemented Dulbecco's Modified Eagles Media (DMEM) at 10,000 cells/well for 24 hours. Cells were treated with the compounds for 24 hours at concentrations ranging from 10 μM to 500 μM. Cells were incubated with MTT reagent for 4 hours followed with MTT detergent for 24 hours. Plates were read on a computerized microplate ELISA reader at an optical density of 570 nm. The percent cytotoxicity was determined by the ratio of treated optical densities to control optical densities (OD) from one and multiplying by 100. The concentration giving 50% cytotoxicity, IC$_{50}$, was determined from the dose response curves for each cell line using the GraphPad Prism software package. Each experiment was performed three separate times and the data presented are the pooled results of the three experiments.

Figure 5:
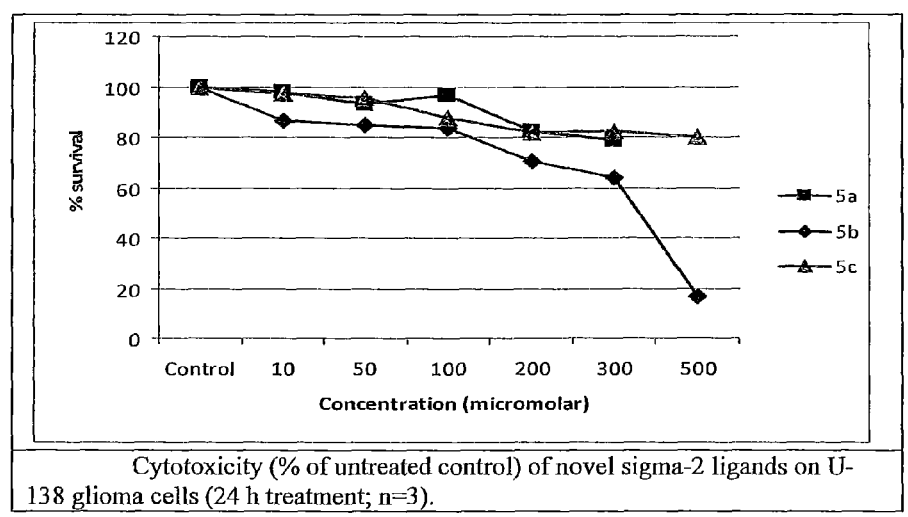
FIG. 5 is a graph depicting the results of an analysis of the effect of compounds 5a, 5b and 5c on cell viability in U-138 glioma cells.
Figure 6:
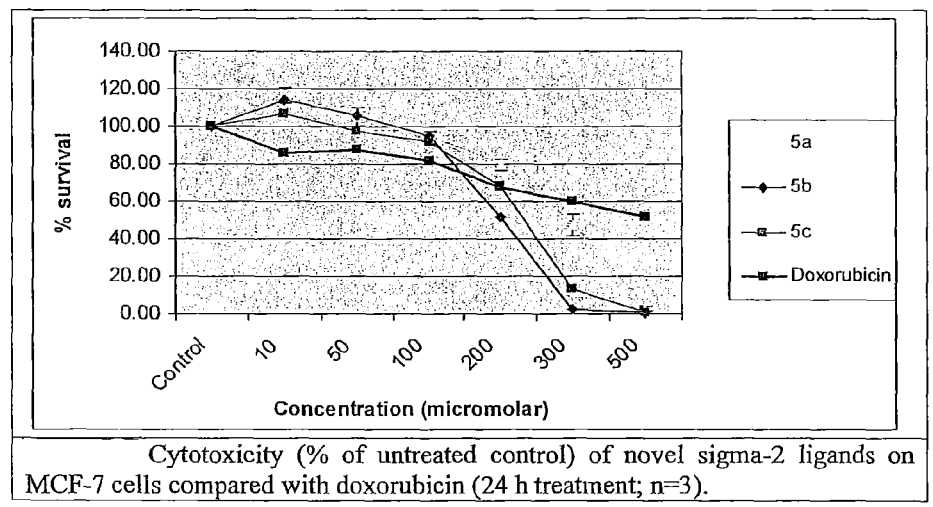
FIG. 6 is a graph depicting the results of an analysis of the effect of compounds 5a, 5b and 5c on cell viability in MCF-7 breast carcinoma cells.

As shown in FIG. 5, compound 5b showed a dose-dependent effect on cell viability in U-138 glioma cells. As shown in FIG. 6, compounds 5a, 5b, and 5c all showed a dose-dependent reduction in cell viability in MCF-7 cells. For example, percent survival rates for compound 5b were 70%, 63%, and 16% of untreated control cells at 200, 300, 500 μM concentrations, respectively.

Example 10

Assay of Compounds 5a, 5b and 5c in a Tonic-Clonic Seizure Model

Compounds 5a, 5b and 5c were evaluated in for the ability to modulate seizures using the Maximal Electroshock Test (MES), a model for generalized tonic-clonic seizures that can provide an indication of a compound's ability to prevent seizure spread when all neuronal circuits in the brain are maximally active. For all tests based on MES convulsions, 60 Hz of alternating current (50 mA in mice) was delivered for 2 s by corneal electrodes which had been primed with an electrolyte solution containing an anesthetic agent (0.5% tetracaine HCL). Mice were tested at various intervals following doses of 30, 100 and 300 mg/kg of test compound given by i.p. injection of a volume of 0.01 mUg. An animal was considered "protected" from MES-induced seizures upon abolition of the hindlimb tonic extensor component of the seizure. Compound 5c was active at 100 and 300 mg/kg.

A number of embodiments of the invention have been described. Nevertheless, it will be understood that various modifications may be made without departing from the spirit and scope of the invention. Accordingly, other embodiments are within the scope of the following claims.

What is claimed is:

1. A compound of Formula I:

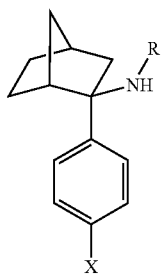

(Formula I)

wherein X is a hydrogen, an alkyl, an alcohol or a halogen; and
R is a 3-(piperidin-1-yl)alkyl group or a 3-(tetrahydro-2H-pyran-2-yloxy)alkyl group.

2. The compound of claim 1, wherein the compound is 2-Phenyl-N-(3-(piperidin-1-yl)propyl)bicyclo[2.2.1]heptan-2-amine.

3. The compound of claim 1, wherein the compound is 2-(4-Fluorophenyl)-N-(3-(piperidin-1-yl)propyl)bicyclo[2.2.1]heptan-2-amine.

4. The compound of claim 1, wherein the compound is 2-(4-Fluorophenyl)-N-(3-(tetrahydro-2H-pyran-2-yloxy)propyl)bicyclo[2.2.1]heptan-2-amine.

5. A compound of Formula II:

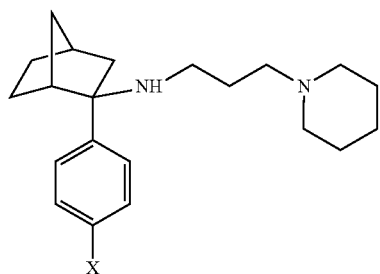

(Formula II)

wherein X is a hydrogen, an alkyl, an alcohol or a halogen.

6. A compound of Formula III:

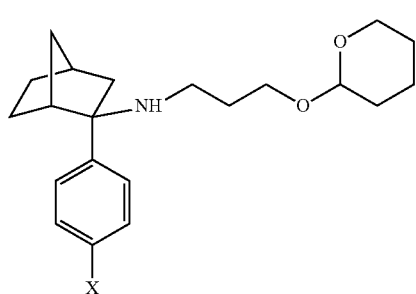

(Formula III)

wherein X is a hydrogen, an alkyl, an alcohol or a halogen.

7. A pharmaceutically acceptable salt of the compound of claim 2.

8. A pharmaceutically acceptable salt of the compound of claim 3.

9. A pharmaceutically acceptable salt of the compound of claim 4.

10. A pharmaceutically acceptable salt of the compound of claim 5.

11. A pharmaceutically acceptable salt of the compound of claim 6.

12. A sigma-2 ligand comprising the compound of claim 1.

13. A sigma-2 ligand comprising the compound of claim 2.

14. A sigma-2 ligand comprising the compound of claim 3.

15. A sigma-2 ligand comprising the compound of claim 4.

16. A sigma-2 ligand comprising the compound of claim 5.

17. A sigma-2 ligand comprising the compound of claim 6.

* * * * *